United States Patent [19]

Babine et al.

[11] Patent Number: 4,800,199

[45] Date of Patent: Jan. 24, 1989

[54] 3-[2-THIAZOLOAMINO]-8-OXO-7-SUBSTITUTED-5-THIA-1-AZABICYCLO-[4.2.0]OCT-2-ENE-2-CARBOXYLIC ACID AND SALTS THEREOF AND DIPHENYLMETHYL ESTERS THEREOF

[75] Inventors: Robert Babine, Pomona; Ving J. Lee, Monsey, both of N.Y.

[73] Assignee: American Cyanamid Company, Stamford, Conn.

[21] Appl. No.: 920,397

[22] Filed: Oct. 20, 1986

[51] Int. Cl.[4] .................. C07D 501/16; A61K 31/545

[52] U.S. Cl. ..................... 514/202; 514/206; 540/222; 540/227; 540/228

[58] Field of Search ............... 540/225, 228, 222, 227; 514/202, 206

[56] References Cited

U.S. PATENT DOCUMENTS 4,504,478  3/1985  Jung et al. ........................ 540/222

*Primary Examiner*—Nicholas S. Rizzo
*Attorney, Agent, or Firm*—Robert P. Raymond

[57] ABSTRACT

Cephalosporins active as antibacterial agents, and processes for synthesis of such agents, are disclosed.

20 Claims, No Drawings

3-[2-THIAZOLOAMINO]-8-OXO-7-SUBSTITUTED-5-THIA-1-AZABICYCLO-[4.2.0]OCT-2-ENE-2-CARBOXYLIC ACID AND SALTS THEREOF AND DIPHENYLMETHYL ESTERS THEREOF

SUMMARY OF THE INVENTION

This invention is concerned with compounds of Formula I:

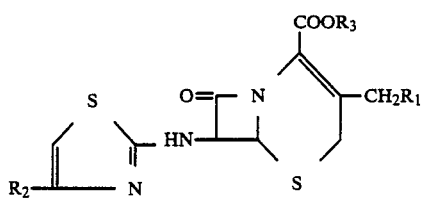

FORMULA I wherein $R_1$ is hydrogen, alkyl($C_1$-$C_3$), vinyl, acetyloxy or

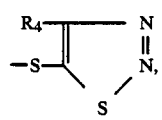

where $R_4$ is hydrogen or alkyl($C_1$-$C_6$); and $R_2$ is alkyl(-$C_1$-$C_3$), phenyl, carboxylic acid, (2,2,2-trichloroethoxy)carbonyl, [2-(trimethylsilyl)ethoxy]carbonyl, phenylmethylamino carbonyl or ethoxycarbonyl and $R_3$ is hydrogen or diphenylmethyl.

The invention is further concerned with processes for the production of compounds of the Formula I as well as their use as intermediates to produce the biologically active compounds of Formula II.

This invention is further concerned with compounds of Formula II:

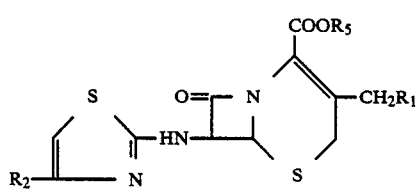

FORMULA II wherein $R_1$ and $R_2$ are as described in Formula I and $R_5$ is hydrogen, an alkali metal or an alkaline earth metal.

This invention is further concerned with processes for the production of compounds of Formula II as well as their use for treating bacterial infections in warm-blooded animals and pharmaceutical compositions of matter containing them.

DESCRIPTION OF THE INVENTION

The compounds of this invention may be prepared according to the following reaction scheme:

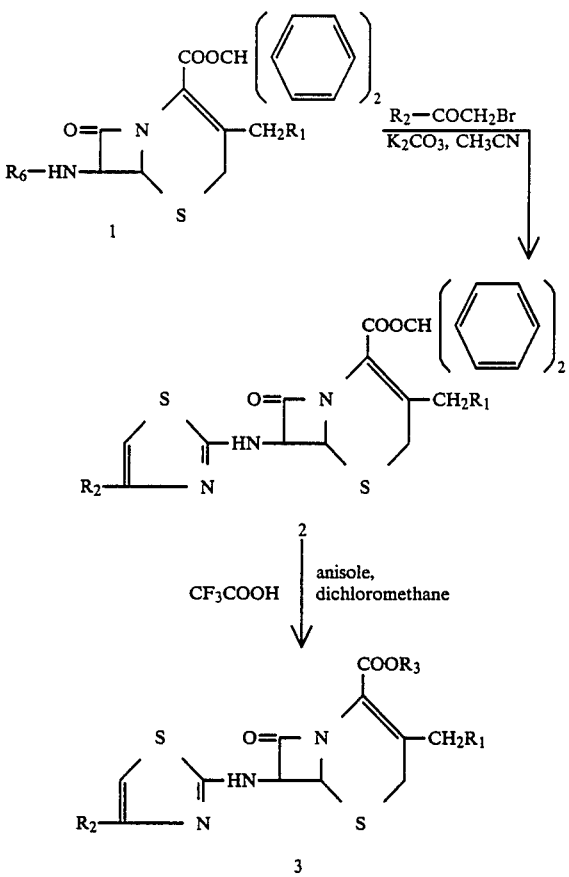

According to the above reaction scheme a 3-substituted-8-oxo-7-[(aminothioxomethyl)amino]-5-thia-1-azabicyclo[4.2.0]oct-2-ene-2-carboxylic acid, diphenylmethyl ester 1, where $R_1$ is as described above and $R_6$ is

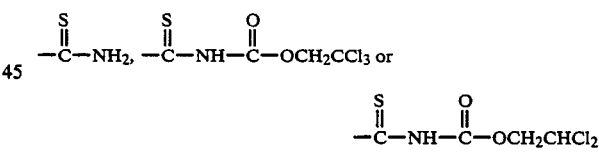

[which are the subject of copending application for U.S. patent Ser. No. 920,398, filed Oct. 20, 1986, filed concurrently herewith, the disclosure and contents thereof being hereby incorporated by reference] is reacted with an α-halogenocarbonyl derivative, where $R_2$ is as described above, and potassium carbonate in acetonitrile, giving diphenylmethyl ester 2 which is then reacted with trifluoroacetic acid and anisole in dichloromethane at 0° C. giving the products 3, where $R_1$ and $R_2$ are as described above and $R_3$ is hydrogen. If $R_3$ is alkali metal or alkaline earth metal, the products 3 are dissolved in water, to which solution an alkali metal bicarbonate or an alkaline earth metal bicarbonate is added, the resulting mixture then being stitted. The water is evaporated, and the desired antibacterial agents where $R_3$ is alkali metal or alkaline earth metal are produced.

The compounds of Formula II of this invention are biologically active and possess potent antibacterial activity when tested by the Mueller-Hinton agar dilution method against a variety of organisms. The results of this test on representative compounds of this invention appear in Table I.

TABLE I

In vitro Antibacterial Activity

Minimal Inhibitory Concentration (mcg/ml)
Compound of Example No.

| Organism | No. 2 | No. 3 | No. 7 | No. 9 | No. 11 | No. 12 |
|---|---|---|---|---|---|---|
| Candida albicans CA 300 | >512 | >512 | — | — | — | — |
| Saccharomyces Y 15 | 128 | 256 | — | — | — | — |
| Mycobacterium smegmatis ATCC 607 | 128 | 256 | — | — | — | — |
| Bacillus subtilis ATCC 6633 | 4 | 8 | 8 | 0.5 | 8 | 1 |
| Bacillus cereus LL No. 4 | 64 | 128 | — | — | — | — |
| Enterococcus OSU 75-1 | 128 | 256 | — | — | — | — |
| Enterococcus CMC 83-53 | — | — | >128 | 64 | >128 | 128 |
| Enterococcus SM 77-15 | 128 | 256 | — | — | — | — |
| Streptococcus faecalis ATCC 29212 | 128 | 256 | >128 | 16 | >128 | 128 |
| Streptococcus mutans ATCC 27352-1 | ≦0.25 | 8 | — | — | — | — |
| Streptococcus mutans BHI (b) | ≦0.25 | 0.5 | — | — | — | — |
| Streptococcus sanguis G-9B (a) | 4 | 1 | — | — | — | — |
| Staphylococcus epidermidis CMC 83-56 | 0.5 | 8 | — | — | — | — |
| Staphylococcus epidermidis CMC 83-133 | — | — | 2 | ≦0.06 | 2 | 2 |
| Staphylococcus epidermidis ATCC 12228 | 0.5 | 16 | 4 | ≦0.06 | 2 | 2 |
| Staphylococcus aureus Smith | 1 | 8 | — | — | — | — |
| Staphylococcus aureus LL No. 14 | 1 | 4 | — | — | — | — |
| Staphylococcus aureus LL No. 27 | 4 | 16 | — | — | — | — |
| Staphylococcus aureus LL No. 45 | 1 | 4 | — | — | — | — |
| Staphylococcus aureus ATCC 25923 | 1 | 8 | 8 | 0.12 | 4 | 4 |
| Staphylococcus aureus SSC 82-31 | — | — | 8 | ≦0.06 | 4 | 4 |
| Staphylococcus aureus SSC 82-20 | — | — | 16 | 0.25 | 8 | 4 |
| Staphylococcus aureus SSC 82-26 | — | — | 8 | 0.12 | 4 | 4 |
| Micrococcus lutea PC 1001 | 4 | 8 | 16 | 1 | 8 | 4 |
| Staphylococcus aureus SSC 82-24 | — | — | >128 | >128 | >128 | 64 |
| Staphylococcus aureus SSC 82-57 | — | — | 128 | 128 | 128 | 128 |
| Escherichia coli 311 | 512 | >512 | >128 | >128 | >128 | 64 |
| Escherichia coli ATCC 25922 | >512 | >512 | >128 | >128 | >128 | >128 |
| Escherichia coli CMC 84-11 | — | — | >128 | >128 | >128 | >128 |
| Klebsiella pneumoniae AD | 512 | >512 | >128 | >128 | >128 | 64 |
| Klebsiella pneumoniae CMC 84-5 | — | — | >128 | >128 | >128 | 128 |
| Klebsiella oxytoca IO 83-1 | — | — | >128 | >128 | >128 | >128 |
| Enterobacter cloacae K79-16 | >512 | >512 | — | — | — | — |
| Enterobacter cloacae CMC 84-4 | — | — | >128 | >128 | >128 | >128 |
| Enterobacter aerogenes IO 83-44 | — | — | >128 | >128 | >128 | >128 |
| Serratia Tul 78-15 | >512 | >512 | — | — | — | — |
| Serratia marcescens CMC 83-27 | — | — | >128 | >128 | >128 | >128 |
| Serratia marcescens F-35 | — | — | >128 | >128 | >128 | >128 |
| Salmonella QHC 77-3 | >512 | >512 | — | — | — | — |
| Proteus morganii K79-25 | >512 | >512 | — | — | — | — |
| Citrobacter freundii K81-28 | 512 | >512 | — | — | — | — |
| Citrobacter freundii IO 83-13 | — | — | >128 | >128 | >128 | >128 |
| Acinetobacter STFD 79-17 | >512 | >512 | — | — | — | — |
| Acinetobacter CMC 83-89 | — | — | >128 | >128 | >128 | >128 |
| Acinetobacter IO 83-49 | — | — | >128 | >128 | >128 | >128 |
| Pseudomonas aeruginosa 12-4-4 | >512 | >512 | >128 | >128 | >128 | >128 |
| Pseudomonas aeruginosa ATCC 27853 | >512 | >512 | >128 | >128 | >128 | >128 |
| Pseudomonas aeruginosa CMC 83-19 | — | — | >128 | >128 | >128 | >128 |
| Proteus rettgheri IO 83-21 | — | — | 128 | 64 | >128 | >128 |
| Morganella morganii IO 83-18 | — | — | >128 | >128 | >128 | >128 |
| Providencia stuartii CMC 83-82 | — | — | >128 | >128 | >128 | >128 |
| Citrobacter diversis K83-24 | — | — | >128 | >128 | >128 | >128 |

The active compounds of Formula II of the present invention are effective in treating bacterial infections in warm-blooded animals when administered in amounts ranging from about 15 mg to about 200 mg per kilogram of body weight per day. A preferred dosage range is from about 20 mg to about 60 mg per kilogram of body weight per day.

These active compounds may be administered by many convenient methods such as orally or parenterally.

A further understanding of the invention can be had from the following non-limiting examples.

EXAMPLE 1

(6R-trans)-3-[(Acetyloxy)methyl]-8-oxo-7-[(4-phenyl-2-thiazolyl)amino]-5-thia-1-azabicyclo[4.2.0]oct-2-ene-2-carboxylic acid, diphenylmethyl ester A mixture of 539 mg of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester, 240 mg of 2-bromo-1-phenylethanone, 85 mg of potassium carbonate and 7 ml of acetonitrile was stirred overnight, then filtered through hydrous magnesium silicate. The filtrate was evaporated, giving 660 mg of the desired compound $[\alpha]_D^{26} = +68° \pm 3°$ (c, 0.4 chloroform).

EXAMPLE 2

(6R-trans)-3-[(Acetyloxy)methyl]-7-[[4-ethoxycarbonyl)-2-thiazolyl]amino]-5-thia-1-azabicyclo[4.2.0]oct-2-ene-2-carboxylic acid, diphenylmethyl ester A mixture of 450 mg of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester, 195 mg of 3-bromo-2-oxopropanoic acid, ethyl ester, 70 mg of potassium carbonate and 7 ml of acetonitrile was stirred overnight and then filtered through hydrous magnesium silicate. The filtrate was evaporated, giving 510 mg of (6R-trans)-3-[acetyloxy)methyl]-7-[[4-(ethoxycarbonyl)-2-thiazolyl]amino]-8-oxo-5-thia-1-azabicyclo[4.2.0]oct-2-ene-2-carboxylic acid, diphenylmethyl ester.

A mixture of 105 mg of the above ester, 0.5 ml of trifluoroacetic acid, 2 drops of anisole and 2 ml of dichloromethane was stirred at 0° C. for 30 minutes, then at room temperature for 30 minutes. The addition of ether and petroleum ether gave a white precipitate. The precipitate was washed with ether and petroleum ether, giving 45 mg of the desired product.

EXAMPLE 3

(6R-trans)-3-[(Acetyloxy)methyl]-8-oxo-7-[(4-phenyl-2-thiazolyl)amino]-5-thia-1-azabicyclo[4.2.0]oct-2-ene-2-carboxylic acid A mixture of 182 mg of (6R-trans)-3-[(acetyloxy)methyl]-8-oxo-7-[(4-phenyl-2-thiazolyl)amino]-5-thia-1-azabicyclo[4.2.0]oct-2-ene-2-carboxylic acid, diphenylmethyl ester, 0.5 ml of trifluoroacetic acid, 3 drops of anisole and 3 ml of dichloromethane was reacted as described in Example 2, giving 92 mg of the desired compound.

EXAMPLE 4

(6R-trans)-3-[(Acetyloxy)methyl]-7-[(4-methyl-2-thiazolyl)amino]-8-oxo-5-thia-1-azabicyclo[4.2.0]oct-2-ene-2-carboxylic acid, diphenylmethyl ester A mixture of 91 mg of (6R-trans)-3-[(acetyloxyl)methyl]-7-[(aminothioxomethyl)amino]-8-oxo-5-thia-1-azabicyclo[4.2.0]oct-2-ene-2-carboxylic acid, diphenylmethyl ester, 33 mg of sodium iodide, 20 mg of potassium carbonate and 2 ml of acetonitrile was reacted as described in Example 2, giving the desired compound.

EXAMPLE 5

(6R-trans)-3-[(Acetyloxy)methyl]-8-oxo-7-[[4-[[2-trimethylsilyl)ethoxy]carbonyl]-2-thiazolyl]amino]-5-thia-1-azabicyclo[4.2.0]oct-2-ene-2-carboxylic acid, diphenylmethyl ester A mixture of 750 mg of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester, 470 mg of 3-bromo-2-oxopropanoic acid, trimethylsilyl ethyl ester, 110 mg of potassium carbonate and 15 ml of acetonitrile was reacted as described in Example 1, giving 850 mg of the desired product.

EXAMPLE 6

(6R-trans)-3-[(Acetyloxy)methyl]-7-[(4-carboxy-2-thiazolyl)amino]-8-oxo-5-thia-1-azabicyclo[4.2.0]oct-2-ene-2-carboxylic acid, diphenylmethyl ester A mixture of 770 mg of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester, 425 mg of 3-bromo-2-oxopropanoic acid, trimethylsilyl ester, 110 mg of potassium carbonate and 15 ml of acetonitrile was reacted as described in Example 1, giving 810 mg of the desired compound.

EXAMPLE 7

(6R-trans)-3-[(Acetyloxy)methyl]-7-[(4-carboxy-2-thiazolyl)amino]-8-oxo-5-thia-1-azabicyclo[4.2.0]oct-2-ene-2-carboxylic acid A mixture of 300 mg of (6R-trans)-3-[(acetyloxy)methyl]-7-[(4-carboxy-2-thiazolyl)amino]-8-oxo-5-thia-1-azabicyclo[4.2.0]oct-2-ene-2-carboxylic acid, diphenylmethyl ester, 1 ml of trifluoroacetic acid, 0.25 ml of anisole and 3 ml of dichloromethane was allowed to stand for 45 minutes, then the solid was collected, washed with ether and petroleum ether and dried, giving 155 mg of the desired compound.

EXAMPLE 8

[2R-(2α,6α,7β,)]3-[(Acetyloxy)methyl]-8-oxo-7-[[4-[(2,2,2-trichloroethoxy)carbonyl]-2-thiazolyl]amino]-5-thia-1-azabicyclo[4.2.0]oct-3-ene-2-carboxylic acid, diphenylmethyl ester A mixture of 1.33 g of (6R-trans)-3-[(acetyloxy)methyl]-7-[(aminothioxomethyl)amino]-8-oxo-5-thia-1-azabicyclo[4.2.0]oct-2-ene-2-carboxylic acid, diphenylmethyl ester, 850 mg of 3-bromo-2-oxopropanoic acid, 2,2,2-trichloroethyl ester, 320 mg of potassium carbonate and 20 ml of acetonitrile was reacted as described in Example 1, giving 350 mg of the desired compound.

EXAMPLE 9

(6R-trans)-3-[(Acetyloxy)methyl]-8-oxo-7-[[4-[(2,2,2-trichloroethoxy)carbonyl]-2-thiazolyl]amino]-5-thia-1-azabicyclo[4.2.0]oct-2-ene-2-carboxylic acid A mixture of 307 mg of [(2R-2α,6α,7β)]-3-[(acetyloxy)methyl]-8-oxo-7-[[4-[(2,2,2-trichloroethoxy)carbonyl]-2-thiazolyl]amino]-5-thia-1-azabicyclo[4.2.0]oct-2-ene-2-carboxylic acid, diphenylmethylester, 1 ml of trifluoroacetic acid, 0.25 ml of anisole and 1 ml of dichloromethane was reacted as described in Example 8, giving 185 mg of the desired product.

EXAMPLE 10

(6R-trans)-3-[(Acetyloxy)methyl]-8-oxo-7-[[4-[[(phenylmethyl)amino]carbonyl]-2-thiazolyl]amino]-5-thia-1-azabicyclo[4.2.0]oct-2-ene-2-carboxylic acid, diphenylmethyl ester A mixture of 176 mg of (6R-trans)-3-[(acetyloxy)methyl]-7-[(4-carboxy-2-thiazolyl)amino]-8-oxo-5-thia-1-azabicyclo[4.2.0]oct-2-ene-2-carboxylic acid, diphenylmethyl ester, 33.3 mg of benzylamine, 79 mg of 2-ethoxy-1(2H)-quinolinecarboxylic acid, ethyl ester and 3 ml of dichloromethane was stirred at room temperature for 1 hour, then added to water and extracted with dichloromethane. The dichloromethane extract was evaporated, giving the desired compound.

EXAMPLE 11

(6R-trans)-3-[(Acetyloxy)methyl]-8-oxo-7-[[4-[[(phenylmethyl)amino]carbonyl]-2-thiazolyl]amino]-5-thia-1-azabicyclo[4.2.0]oct-2-ene-2-carboxylic acid A mixture of 175 mg of (6R-trans)-3-[(acetyloxy)methyl]-8-oxo-7-[[4-[[(phenylmethyl)amino]carbonyl]-2-thiazolyl]amino]-5-thia-1-azabicyclo[4.2.0]oct-2-ene-2- carboxylic acid, diphenylmethyl ester, trifluoroacetic acid and anisole in dichloromethane was stirred for 45 minutes. The addition of dichloromethane, ether and petroleum ether caused precipitation. The solid was collected and washed with ether and petroleum ether, giving 105 mg of the desired product.

EXAMPLE 12

(6R-trans)-3-[(Acetyloxy)methyl]-7-[(4-methyl-2-thiazolyl)amino]-8-oxo-5-thia-1-azabicyclo[4.2.0]oct-2-ene-2-carboxylic acid A mixture of 210 mg of (6R-trans)-3-[(acetyloxy)methyl]-7-[(4-methyl-2-thiazolyl)amino]-8-oxo-5-thia-1-azabicyclo[4.2.0]oct-2-ene-2-carboxylic acid, diphenylmethyl ester, trifluoroacetic acid and anisole in dichloromethane was reacted as described in Example 11, giving 123 mg of the desired product.

What is claimed is:

1. A compound selected from those of the formula:

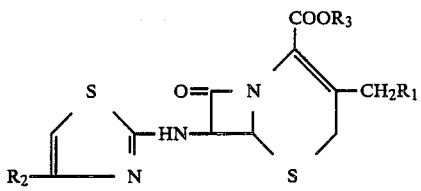

wherein $R_1$ is hydrogen, alkyl($C_1$–$C_3$), vinyl, acetyloxy or

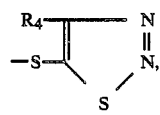

where $R_4$ is hydrogen or alkyl($C_1$–$C_6$); $R_2$ is alkyl($C_1$–$C_3$), phenyl, carboxylic acid, (2,2,2-trichloroethoxy)carbonyl, [2-trimethylsilyl)ethoxy]carbonyl, phenylmethylamino carbonyl or ethoxycarbonyl; and $R_3$ is hydrogen or diphenylmethyl.

2. The compound according to claim 1, (6R-trans)-3-[(acetyloxy)methyl]-8-oxo-7-[(4-phenyl-2-thiazolyl)amino]-5-thia-1-azabicyclo[4.2.0]oct-2-ene-2-carboxylic acid, diphenylmethyl ester.

3. The compound according to claim 1, (6R-trans)-3-[(acetyloxy)methyl]-7-[(4-methyl-2-thiazolyl)amino]-8-oxo-5-thia-1-azabicyclo[4.2.0]oct-2-ene-2-carboxylic acid, diphenylmethyl ester.

4. The compound according to claim 1, (6R-trans)-3-[(acetyloxy)methyl]-7-[(4-methyl-2-thiazolyl)amino]-8-oxo-5-thia-1-azabicyclo[4.2.0]oct-2-ene-2-carboxylic acid, diphenylmethyl ester, 5-oxide.

5. The compound according to claim 1, (6R-trans)-3-[(acetyloxy)methyl]-8-oxo-7-[[4-[[2-(trimethylsilyl)ethoxy]carbonyl]-2-thiazolyl]amino]-5-thia-1-azabicyclo[4.2.0]oct-2-ene-2-carboxylic acid, diphenylmethyl ester.

6. The compound according to claim 1, (6R-trans)-3-[(acetyloxy)methyl]-7-[[4-carboxy-2-thiazolyl)amino]-8-oxo-5-thia-1-azabicyclo[4.2.0]oct-2-ene-2-carboxylic acid, diphenylmethyl ester.

7. The compound according to claim 1, [(2R-(2α,6α,7β)]-3-[(acetyloxy)methyl]-8-oxo-7-[[4-[(2,2,2-trichloroethoxy)carbonyl]-2-thiazolyl]amino]-5-thia-1-azabicyclo[4.2.0]oct-2-ene-2-carboxylic acid, diphenylmethyl ester.

8. The compound according to claim 1, (6R-trans)-3-[(acetyloxy)methyl]-8-oxo-7-[[4-[[(phenylmehtyl)amino]carbonyl]-2-thiazolyl]amino]-5-thia-1-azabicyclo[4.2.0]oct-2-ene-2-carboxylic acid, diphenylmethyl ester.

9. The compound according to claim 1, (6R-trans)-3-[(acetyloxy)methyl]-8-oxo-7-[[4-[[(phenylmethyl)amino]carbonyl-2-thiazolyl]amino]-5-thia-1-azabicyclo[4.2.0]oct-2-ene-2-carboxylic acid.

10. The compound according to claim 1, (6R-trans)-3-[(acetyloxy)methyl]-7-[(4-methyl-2-thiazolyl)amino]-8-oxo-5-thia-1-azabicyclo[4.2.0]oct-2-ene-2-carboxylic acid.

11. A compound selected from those of the formula:

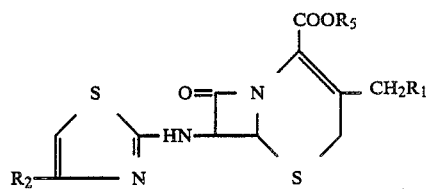

wherein $R_1$ is hydrogen, alkyl($C_1$–$C_3$), vinyl, acetyloxy or

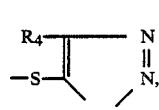

where $R_4$ is hydrogen or alkyl($C_1$–$C_6$); $R_2$ is alkyl($C_1$–$C_3$), phenyl, carboxylic acid, (2,2,2-trichloroethoxy)carbonyl, [2-(trimethylsilyl)ethoxy]carbonyl, phenylmethylamino carbonyl or ethoxy carbonyl; and $R_5$ is hydrogen, an alkali metal or an alkaline earth metal.

12. The compound according to claim 11, (6R-trans)-3-[(acetyloxy)methyl]-7-[[4-ethoxycarbonyl)-2-thiazolyl]amino]-8-oxo-5-thia-1-azabicyclo[4.2.0]oct-2-ene-2-carboxylic acid.

13. The compound according to claim 11, (6R-trans)-3-[(acetyloxy)methyl]-8-oxo-7-[(4-phenyl-2-thiazolyl)amino]-5-thia-1-azabicyclo[4.2.0]oct-2-ene-2-carboxylic acid.

14. The compound according to claim 11, (6R-trans)-3-[(acetyloxy)methyl]-7-[(4-carboxy-2-thiazolyl]amino]-8-oxo-5-thia-1-azabicyclo[4.2.0]oct-2-ene-2-carboxylic acid.

15. The compound according to claim 11, (6R-trans)-3-[(acetyloxy)methyl]-8-oxo-7-[[4-[(2,2,2-trichloroethoxy)carbonyl]-2-thiazolyl)amino]-5-thia-1-azabicyclo[4.2.0]oct-2-ene-2-carboxylic acid.

16. A method for treating bacterial infections in warm-blooded animals which comprises administering to said animals an antibacterially effective amount of a compound selected from those of the formula:

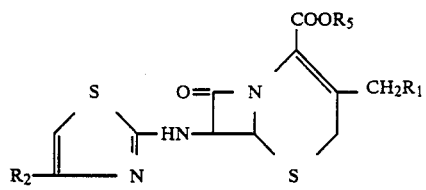

wherein $R_1$ is hydrogen, alkyl($C_1$–$C_3$), vinyl, acetyloxy or

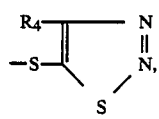

where $R_4$ is hydrogen or alkyl($C_1$–$C_6$); $R_2$ is alkyl(-$C_1$–$C_3$), phenyl, carboxylic acid, (2,2,2-trichloroethoxy)carbonyl, [2-(trimethylsilyl)ethoxy]carbonyl, phenylmethylamino carbonyl or ethoxycarbonyl; and $R_5$ is hydrogen, an alkali metal or an alkaline earth metal.

17. A composition of matter for treating bacterial infections in warm-blooded animals which comprises from about 15 mg to about 200 mg of a compound of the formula

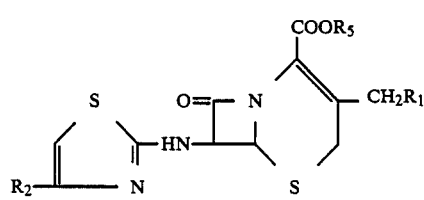

wherein $R_1$ is hydrogen, alkyl($C_1$–$C_3$), vinyl, acetyloxy or

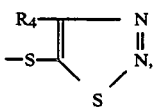

where $R_4$ is hydrogen or alkyl($C_1$–$C_6$); $R_2$ is alkyl(-$C_1$–$C_3$), phenyl, carboxylic acid, (2,2,2-trichloroethoxy)carbonyl, (2-(trimethylsilyl)ethoxy)carbonyl, phenylmethylamino carbonyl or ethoxycarbonyl; and $R_5$ is hydrogen, an alkali metal or an alkaline earth metal; in association with a pharmaceutically acceptable carrier in dosage unit form.

18. A process for producing a compound of the formula:

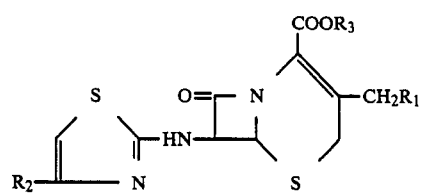

wherein $R_1$ is hydrogen, alkyl($C_1$–$C_3$), vinyl, acetyloxy or

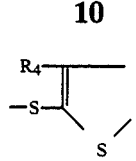

where $R_4$ is hydrogen or alkyl($C_1$–$C_6$); $R_2$ is alkyl(-$C_1$–$C_3$), phenyl, carboxylic acid, (2,2,2-trichloroethoxy)carbonyl, [2-(trimethylsilyl)ethoxy]carbonyl, phenylmethylamino carbonyl or ethoxycarbonyl; and $R_3$ is hydrogen, an alkali metal or an alkaline earth metal; which comprises reacting a 3-substituted-8-oxo-7-substituted-thioxomethylamino-5-thia-1-azabicyclo[4.2.0]oct-2-ene-2-carboxylic acid, diphenylmethyl ester of the formula

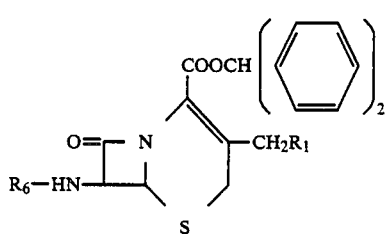

where $R_1$ is as described above and $R_6$ is

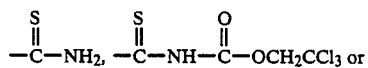

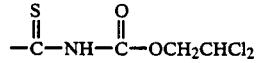

with an α-halogenocarbonyl derivative of the formula $R_2COCH_2Br$, where $R_2$ is as described above, and potassium carbonate in acetonitrile, giving a compound of the formula

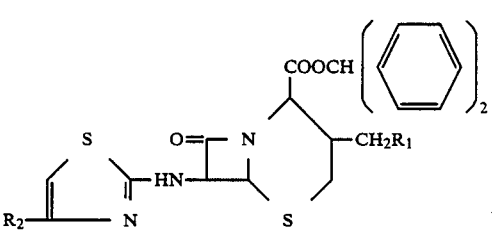

where $R_1$ and $R_2$ are as described above, followed by reaction with trifluoroacetic acid and anisole in dichloromethane at −5° to 45° C., giving the desired antibacterial agents where $R_3$ is hydrogen, and dissolving said resulting antibacterial agent in water, adding an alkali metal bicarbonate, stirring and then evaporating the water to produce the desired antibacterial agents where $R_3$ is alkali metal or alkaline earth metal.

19. A compound of the formula

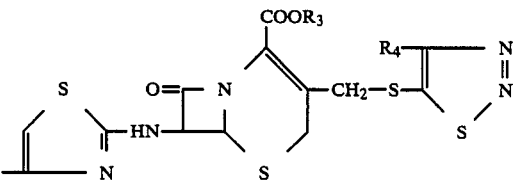

wherein $R_4$ is hydrogen or alkyl ($C_1$–$C_6$), $R_2$ is alkyl ($C_1$–$C_3$), phenyl, carboxylic acid, (2,2,2-trichloroethoxy)carbonyl, [2-(trimethylsilyl)ethoxy]carbonyl, phenylmethylaminocarbonyl, or ethoxycarbonyl; and $R_3$ is hydrogen or diphenylmethyl.

20. A compound according to claim 19, wherein $R_2$ is alkyl ($C_1$–$C_3$).

* * * * *